United States Patent [19]

Mizuno et al.

[11] 4,094,905
[45] June 13, 1978

[54] PROCESS FOR PRODUCING DIMETHYL FORMAMIDE

[75] Inventors: Kinichi Mizuno; Masao Saito; Yuzi Onda; Tetsuo Aoyama; Kumiko Kato, all of Niigata, Japan

[73] Assignee: Mitsubishi Gas Chemical Company, Ltd, Tokyo, Japan

[21] Appl. No.: 802,524

[22] Filed: Jun. 1, 1977

[30] Foreign Application Priority Data

Jun. 10, 1976 Japan .................. 51-68122

[51] Int. Cl.$^2$ ........................................... C07C 102/00
[52] U.S. Cl. ............................................... 260/561 R
[58] Field of Search .................................. 260/561 R

[56] References Cited

U.S. PATENT DOCUMENTS

| | | | |
|---|---|---|---|
| 2,677,706 | 5/1954 | Giachino | 260/561 R |
| 3,072,725 | 1/1963 | Surman | 260/561 R |
| 3,347,916 | 10/1967 | Huber | 260/561 R |
| 3,412,151 | 11/1968 | Nozaki | 260/561 R |
| 3,446,842 | 5/1969 | Nozaki | 260/561 R |
| 4,042,621 | 8/1977 | Saver | 260/561 R |

FOREIGN PATENT DOCUMENTS 863,800  12/1952  Germany.

*Primary Examiner*—Arthur P. Demers
*Attorney, Agent, or Firm*—Armstrong, Nikaido, Marmelstein & Kubovcik

[57] ABSTRACT

Dimethyl formamide is produced in high yield with high selectivity by reaction of monomethyl formamide with trimethylamine and carbon monoxide in the presence of a catalyst such as halogen elements, halides, inorganic acids, solid acids and metal carbonyls at a temperature of 150° to 300° C under a pressure of 20 kg/cm$^2$ gage or higher.

12 Claims, No Drawings

PROCESS FOR PRODUCING DIMETHYL FORMAMIDE

This invention relates to a novel process for producing dimethyl formamide by making monomethyl formamide react with trimethylamine and carbon monoxide in the presence of a catalyst.

Conventionally, dimethyl formamide is produced by making dimethylamine react with carbon monoxide or methyl formate. Dimethylamine as a raw material in said conventional process is produced usually by dehydration reaction of methyl alcohol and ammonia, but a large amount of monomethylamine and trimethylamine is inevitably by-produced at the same time in the production of dimethylamine. However, commercial demands for monomethylamine and trimethylamine are poor, as compared with that for dimethylamine, and most of these two by-produced amines are usually recycled to methylamine synthesis system, and converted to dimethylamine. Therefore, use of monomethylamine and trimethylamine having less commercial demands as the raw material for dimethyl formamide in place of dimethylamine is expected to bring about a remarkable rationalization to the methylamine industry and also a great commercial significance.

To meet such expectation, U.S. Pat. No. 2,677,706 proposes a process for producing dimethyl formamide by making monomethylamine and/or dimethylamine or further together with trimethylamine react with carbon monoxide in the presence of cuprous chloride, cupric chloride, ammonium chloride, potassium acetate or boron trifluoride as a catalyst. However, the proposed process has low selectivities of monomethylamine and trimethylamine to dimethyl formamide, and thus is not satisfactory as a commercial process.

As a result of extensive studies of the process for producing dimethyl formamide from monomethylamine or trimethylamine as a raw material, the present inventors have found a process for producing dimethyl formamide in high yield by making monomethyl formamide, which can be readily prepared by reaction of monomethylamine with carbon monoxide or methyl formate, react with trimethylamine and carbon monoxide.

That is, the present invention provides a novel process for producing dimethyl formamide from monomethyl formamide, trimethylamine and carbon monoxide as raw materials. In the present invention, it is presumed that reaction of the following reaction formula takes place.

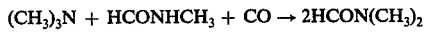

$$(CH_3)_3N + HCONHCH_3 + CO \rightarrow 2HCON(CH_3)_2$$

The reaction is carried out under a pressure of 20 kg/cm$^2$ gage or higher, preferably 30 to 600 kg/cm$^2$ gage. The reaction can proceed under a lower pressure than 20 kg/cm$^2$ gage, but side reactions are readily promoted, and the process becomes unpractical. A pressure higher than 600 kg/cm$^2$ gage is useful to carry out the reaction of the present invention, but not practical in view of economy of the process.

The reaction is carried out at a temperature of 150° to 300° C, preferably 160° to 280° C. A temperature outside said range should be avoided on account of the reaction rate and selectivity.

Ratio by mole of trimethylamine to monomethyl formamide is 0.1 to 10, preferably 0.5 to 5. A ratio outside said range will increase the amount of unreacted raw materials, and is not economical.

Carbon monoxide is a raw material and also plays a role of maintaining the reaction pressure in the present invention, and thus must be used in much excess. But a gas mixture of carbon monoxide and an inert gas can be used on condition that the partial pressure of carbon monoxide is higher than 10 kg/cm$^2$ gauge.

The reaction proceeds without a catalyst, but a catalyst is economically indispensable for the present process. Catalysts effectively used in the reaction of the present invention include halogen elements such as fluorine, chlorine, bromine, iodine, etc.; halides such as metal halides, ammonium halides, hydrohalogenic acids, alkyl halides, etc.; inorganic acids such as boric acid, sulfuric acid, phosphoric acid, etc., solid acids such as silca-alumina, etc., metal carbonyls such as carbonyls of iron, cobalt, nickel, rhodium and ruthenium. Among these catalysts, halogen elements, halides and metal carbonyls are preferable, and iron carbonyl is more preferable.

The catalysts can be used alone or in a combination of two or more of these. In the case of the metal carbonyls as the catalyst, it is not always necessary to add the metal carbonyl to the reaction system, and addition of a metal or metal compound capable of being converted to the metal carbonyl under the reaction conditions of the present process, such as iron, cobalt, nickel, rhodium and ruthenium and their oxides, hydroxides and salts of organic or inorganic acid such as oxalate, naphthenate, sulfate, nitrate and carbonate, is effective.

The halogen element and the halide as the catalyst are used in an amount of 0.1 to 350 mg-atoms, preferably 1 to 300 mg-atoms, in terms of halogen per mole of monomethyl formamide.

The inorganic acid and metal carbonyl as the catalyst is used in an amount of 0.1 to 350 mg-moles, preferably 1 to 300 mg-moles per mole of monomethyl formamide.

The solid acid as the catalyst is used in an amount of 0.1 to 50 g, preferably 1 to 30 g, per mole of monomethyl formamide.

When the amount of the catalyst used is smaller than the lower limit of said ranges, the yield of dimethyl formamide is decreased, whereas when the amount of the catalyst is larger than the upper limit of said ranges, hydrogen, carbon dioxide and methane are readily by-produced.

The reaction can be carried out in any manner, for example, batchwise or continuously.

According to the present invention, dimethyl formamide can be produced in high yield with high selectivity. Furthermore, monomethyl formamide, one of the raw materials used in the present invention, can be readily prepared from monomethylamine and carbon monoxide or methyl formate. Therefore, by adopting a manner that monomethyl formamide is prepared, first of all, from these materials, and the resulting monomethyl formamide is used as the raw material of the present invention, both monomethylamine and trimethylamine having less commercial demands, among three amines formed from methanol and ammonia, can be effectively utilized to produce dimethyl formamide. That is, the present invention has a very important commercial significance in this respect. Of course, monomethyl formamide obtained according to other processes can be used as the raw material in the present invention.

Now, the present invention will be described below in detail, referring to Examples.

In the examples, dimethyl formamide yield to monomethyl formamide and selectivity of monomethyl formamide to dimethyl formamide are calculated according to aforementioned reaction formula.

EXAMPLES 2 – 18

Reaction was carried out in the same manner as in Example 1, changing ratios by mole of the raw materials, kind and amount of the catalyst, temperature, and pressure. The results are shown in the following table together with the results of Example 1.

Table

| Example No. | 1 | 2 | 3 | 4 | 5 | 6 | 7 | 8 | 10 |
|---|---|---|---|---|---|---|---|---|---|
| Catalyst |  |  |  |  |  |  |  |  |  |
| Kind | $I_2$ | $I_2$ | $I_2$ | $I_2$ | $TiI_4$ | conc. $H_2SO_4$ | $Br_2$ | $NH_4I$ | 36% HCl |
| Amount(g) | 1.6 | 0.8 | 0.8 | 2.1 | 0.85 | 0.85 | 0.5 | 0.9 | 0.6 |
| Monomethyl formamide (g) | 10.0 | 10.0 | 5.0 | 5.0 | 10.0 | 10.0 | 9.9 | 10.2 | 9.9 |
| Trimethylamine (g) | 10.0 | 10.0 | 15.5 | 15.0 | 10.0 | 10.0 | 10.3 | 10.1 | 10.5 |
| Pressure of CO charged ($kg/cm^2$ gage) | 95 | 145 | 95 | 140 | 95 | 90 | 93 | 92 | 90 |
| Maximum CO pressure ($kg/cm^2$ gage) | 236 | 340 | 242 | 312 | 245 | 234 | 233 | 232 | 245 |
| CO pressure at end of reaction ($kg/cm^2$ gage) | 77 | 125 | 81 | 120 | 93 | 87 | 93 | 84 | 88 |
| Reaction temperature (° C) | 260 | 255 | 260 | 220 | 265 | 265 | 265 | 259 | 265 |
| Reaction time (hr) | 4 | 4 | 4 | 4 | 4 | 4 | 4 | 4 | 4 |
| Monomethyl formamide conversion (%) | 82.1 | 74.5 | 90.7 | 95.2 | 79.0 | 41.2 | 71.6 | 75.5 | 56.0 |
| Dimethyl formamide yield (g) | 15.0 | 14.1 | 8.7 | 9.7 | 12.2 | 5.4 | 10.0 | 13.4 | 8.8 |
| Dimethyl formamide yield to monomethyl formamide (%) | 60.6 | 57.0 | 70.3 | 78.4 | 49.3 | 21.8 | 40.8 | 53.1 | 35.9 |
| Selectivity of monomethyl formamide to dimethyl formamide (%) | 73.8 | 76.5 | 77.5 | 82.3 | 62.4 | 53.0 | 57.0 | 70.3 | 64.1 |

Note:
*$Al_2O_3$ 13 %
(a) $FeC_2O_4 \cdot 2H_2O$
(b) $(NH_4)_3Fe(C_2H_4)_3 \cdot 3H_2O$

| 10 | 11 | 12 | 13 | 14 | 15 | 16 | 17 | 18 |
|---|---|---|---|---|---|---|---|---|
| Silica-alumina* | $Co_2(CO)_8$ | $CH_3I$ | $Fe(CO)_5$ | (a) | (b) | $Fe_2O_3$ | $FeSO_4$ |  |
| 2 | 1 | 1.1 | 1.3 | 1.2 | 2.8 | 0.5 | 0.4 | 1.1 |
| 10.3 | 10.0 | 9.8 | 10.7 | 10.2 | 10.2 | 10.6 | 10.6 | 10.6 |
| 10.4 | 10.3 | 9.8 | 10.3 | 10.3 | 9.8 | 10.6 | 10.6 | 10.6 |
| 100 | 92 | 92 | 90 | 90 | 99 | 92 | 90 | 90 |
| 248 | 234 | 229 | 250 | 250 | 270 | 250 | 250 | 250 |
| 107 | 85 | 83 | 81 | 82 | 93 | 84 | 85 | 85 |
| 265 | 260 | 260 | 248 | 239 | 238 | 250 | 240 | 240 |
| 4 | 4 | 4 | 4 | 4 | 4 | 4 | 4 | 4 |
| 44.0 | 58.2 | 76.4 | 91.1 | 65.1 | 48.3 | 86.1 | 51.7 | 50.4 |
| 4.4 | 9.7 | 12.2 | 14.6 | 12.7 | 6.6 | 13.1 | 7.8 | 8.0 |
| 17.3 | 39.2 | 50.3 | 55.1 | 50.3 | 26.1 | 49.9 | 29.7 | 30.5 |
| 39.2 | 67.3 | 65.8 | 60.5 | 77.3 | 54.1 | 58.0 | 57.5 | 60.5 |

REFERENCE EXAMPLE

Monomethylamine was made to react with carbon monoxide under a reaction pressure of 20 $kg/cm^2$ gage at a reaction temperature of 75° C, using 40 mg-atoms of sodium methylate in terms of sodium per mole of monomethylamine, whereby monomethyl formamide was obtained in yield of 97%.

EXAMPLE 1

10 Grams of monomethyl formamide obtained in Reference Example, 10 g of trimethylamine, and 1.6 g of iodine as catalyst were charged into an autoclave having a capacity of 100 ml, and carbon monoxide was charged to the autoclave under pressure up to 95 $kg/cm^2$ gage. Reaction was conducted at a temperature of 260° C for 4 hours. Maximum pressure during the reaction was 236 $kg/cm^2$ gage, and pressure at the end of reaction was 77 $kg/cm^2$ gage. Products were analyzed by gas chromatography. 82.1% of monomethyl formamide charged was converted, and 15.0 g of dimethyl formamide was obtained.

Dimethyl formamide yield to monomethyl formamide was 60.6%, and selectivity of monomethyl formamide to dimethyl formamide was 73.8%.

What is claimed is:

1. A process for producing dimethyl formamide, which comprises making monomethyl formamide react with trimethylamine and carbon monoxide in the presence of a catalyst.

2. A process according to claim 1, wherein the catalyst is at least one of halogen elements, halides, inorganic acids, solid acids, and metal carbonyls.

3. A process according to claim 2, wherein 0.1 to 350 mg-atoms in terms of halogen of the halogen elements or halides is used as the catalyst per mole of monomethyl formamide.

4. A process according to claim 2, wherein 0.1 to 350 mg-moles of the inorganic acid or metal carbonyls is used as the catalyst per mole of monomethyl formamide.

5. A process according to claim 2, wherein 0.1 to 50 g of the solid acid is used as the catalyst per mole of monomethyl formamide.

6. A process according to claim 2, wherein the catalyst is at least one of halogen elements, halides and metal carbonyls.

7. A process according to claim 1, wherein the trimethyl amine is used in a ratio by mole of trimethylamine to monomethyl formamide of 0.1 to 10.

8. A process according to claim 1, wherein the carbon monoxide is used in much excess.

9. A process according to claim 1, wherein the reaction is carried out under a pressure of 20 kg/cm² gage, or higher.

10. A process according to claim 1, wherein the reaction is carried out at a temperature of 150° to 300° C.

11. A process according to claim 1, wherein monomethyl formamide prepared by reaction of monomethylamine with carbon monoxide or methyl formate is used as the monomethyl formamide.

12. A process according to claim 2, wherein a metal carbonyl is added as a metal or metal compound capable of being converted to the metal carbonyl under reaction conditions.

* * * * *

UNITED STATES PATENT AND TRADEMARK OFFICE
CERTIFICATE OF CORRECTION

PATENT NO. : 4,094,905
DATED : June 13, 1978
INVENTOR(S) : KINICHI MIZUNO ET AL

It is certified that error appears in the above-identified patent and that said Letters Patent are hereby corrected as shown below:

Title page, delete the name of the assignee and substitute therefor --Mitsubishi Gas Chemical Company, Inc.--

In the Table, Cols. 3 and 4 of the patent, following "Example No.", delete the figure "10" and substitute --9--.

In the Footnote of the Table, delete formula (b) and insert --(b) $(NH_4)_3 Fe(C_2O_4)_3 \cdot 3H_2O$--.

Delete "$FeSO_4$" under Heading No. 17; under Heading No. 18, insert --$FeSO_4$--; in place of "$FeSO_4$" under Heading No. 17, insert --Fe--.

Signed and Sealed this

Twenty-ninth Day of May 1979

[SEAL]

Attest:

RUTH C. MASON
Attesting Officer

DONALD W. BANNER
Commissioner of Patents and Trademarks